June 2, 1964 A. PERELLI-MINETTI Plant Pat. 2,408
GRAPE VINE
Filed Dec. 22, 1961
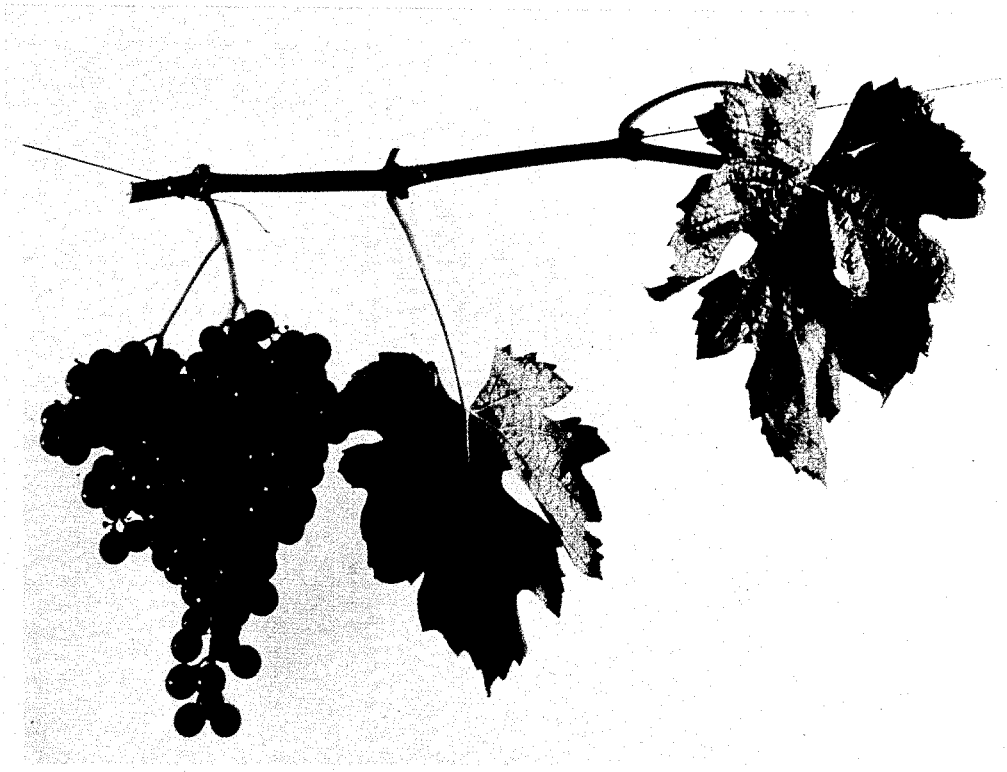
INVENTOR
ANTONIO PERELLI-MINETTI
by Miketta & Glenny
ATTORNEYS.

United States Patent Office

Plant Pat. 2,408
Patented June 2, 1964

2,408
GRAPE VINE

Antonio Perelli-Minetti, P.O. Box 817, Delano, Calif.

Filed Dec. 22, 1961, Ser. No. 161,755
1 Claim. (Cl. Plt.—47)

The subject matter of this application for plant patent is a new and distinct variety of the genus Vitis which, although edible, is particularly valuable and useful as a wine grape.

Although California is well known for its wines, the soil and climatic conditions of the southern portion of the State, including the San Joaquin Valley, produce grapes which have a relatively low acid content; wines made therefrom tend to be flat and lack stability. Vintners have long sought a grape vine which would bear heavily, have adequate foliage to protect the grape clusters, be resistant to rain, whose clusters and bunches would not be susceptible to bunch rot and be unaffected by frost when ready to be picked and bear grapes producing a juice having both a high sugar and a high acid content with good flavor and color. The grape vine and grapes forming the subject matter hereof, although not resistant to phylloxera and mildew, appear to have more than substantially all desired characteristics.

The grape vine of the present invention originated as an observed sport runner on one of several hundred seedlings (of non-recorded species and variety) raised on Delano loam in the San Joaquin Valley of the State of California. It was asexually reproduced by grafting upon Verdiso root stock and by propagation of cuttings therefrom. The appended drawing (color photograph) illustrates the new variety and exemplifies a main runner carrying a grape cluster and representative foliage.

The new variety herein disclosed is readily propagated from cuttings and may be grafted upon various root stocks. The vine starts to leaf slightly later than other varieties (in the Fresno-Bakersfield area of the San Joaquin Valley), blooms in May and the grapes are usually ready for picking from late in October to the middle of November.

The foilage is prolific, and extends from nodes which are not excessively spaced. Effective shading of the grape clusters is facilitated by the tendency of the vine to grow many side shoots or branches from the main runners. The vine tends to send out a larger number of side runners than other varieties. Veining is readily visible upon the upper surface of the leaves and extends above the lighter colored, less glossy, lower surface. Mature leaves may be said to have coloration which varies from that shown on Plate 23A6 to Plate 23L10 (including Empire Green and Pogo Green) and from Plate 24C11 to Plate 24L10 (including Hunter Green). References are to plates of the "Dictionary of Color" by Maerz and Paul, 1st edition, McGraw Hill Book Co. Spring and early summer foliage contains more green; a reddish component appears to be introduced in later summer and becomes more pronounced after the first cold weather. The lower surface is matt in appearance and its color varies (on different mature leaves) from I–1, I–4, H–2 and B–8 to K–9 on Plate 22. Some lower surfaces of younger leaves may resemble Plate 15J1 and L1.

It may be observed that the leaves on the main runners or shoots are deeply cleft or indented, two such deep indentations appearing on each side of the main stem vein. It has been observed that the leaves carried by the side shoots or branches (secondary growth) do not exhibit the four clefts and five lobes; in some instances the outer pair of indentations is present in a partly developed form, but the inner pair (closer to the stem) is lacking, thereby giving the leaf a more circular or rounded, orbiculate appearance. All leaves have apiculate tips, cordate bases and serrated or incised margins.

The vine is very prolific and bears numerous shapely bunches of grapes on its main and secondary runners. The bunches on the main runners are rather uniform in size, and weigh between about 1 lb. and 1.4 lbs., each; the 2nd growth bunches of grapes are individually much smaller and more loose and comprise a minor proportion of the total productive output. Well-established vines should produce 12 to 15 tons of grapes per acre.

The individual berries are rather small and round, with a diameter of about 0.5 inch. The skin is of medium thickness and is practically black (with a barely perceptible red component) when the surface bloom is rubbed off. The color of the bloom is exemplified by Plate 38C4, 5, 6 and F4. Seed content is relatively low, averaging less than two per berry, and the seeds are not large.

One of the characteristics of this variety is the resistance of the grapes to bunch rot, to rain and to frost damage at maturity. Even the second crop of bunches on the side shoots may be gathered if the season extends beyond an early frost (which may defoliate the vines) and will not cause excessive damage to the grapes, since they are able to stay on the vines and will not drop off because of such frost; they have been effectively picked and used three or four weeks after such frost.

The most important characteristics of this new variety are of interest to the vintner. The juice expressed from the light colored meat of these grapes is white-gray in color and has a distinctive fresh fruity flavor. The distinctive flavor is apparently due to a high content of acids and volatile aromatics. It has been described as suggesting pear-like and raspberry-like flavors. The freshness of the flavor is stimulated by the high acid content of the juice, concurrently with the high sugar content.

The skin of these grapes imparts a deep, intense red coloration to juice produced by crushing and macerating whole grapes, which color is intensified by fermentation. As a result, a dark red juice is consistently obtained which has a high sugar content, the juice containing over 22% and often as high as 26% or 28% of sugar (Balling test) and concurrently a low pH (high total acid content) due to the presence of 0.8 to 1.2 gr. of free acid (as tartaric) per 100 ml. The intense red color is apparently substantially free from blue components since the white foam obtained by checking a sample of juice does not carry a bluish tinge. Thin layers of such juice appear bright red to transmitted light somewhat similar to Plate 3L6 or Plate 4L6 (including Salvia and Red Cross).

The flavor, color and acidity render the juice extremely palatable and pleasing to the taste and eye; the desirable attributes persist in wine made from such juice. The juice and wine are extremely useful in blending with other juices and wines. Juice from the grapes herein described, when concentrated, shipped to other wineries, reconstituted, blended and fermented, produces wines of better flavor and color. The red color of the concentrated juice is very stable and does not brown appreciably even upon storage for a year. The flavor of the juice is very distinctive and when blended with other juices and converted to wine, can be discerned by a wine taster when present in a concentration as low as 15% or 20%. The acid content freshens and enhances the flavor of normally flat wines.

The wine made by normal fermentation from the juice of these grapes will show a decided, intense red color. When such wine is placed in a glass and shaken, a foam is produced which will remain for hours before vanishing and which will have and maintain the red coloring in such foam. Such stable red foam is not duplicated by any other wines or juices derived from other grapes. Wines made from the juice of the grape of this invention will exhibit the intense red and stable foam even when the wine is a year old, whereas red wines of similar ages but made from other grapes will produce a practically colorless or white foam which disappears quickly.

I claim:

A new and distinct variety of grape vine substantially as shown and described, characterized by the presence of main runners bearing leaves having four axially symmetrically disposed clefts, such leaves having sharp tips and serrated margins between clefts, and by the presence of secondary branches extending from the main runners, said secondary branches having substantially orbiculate leaves with pointed tips and serrated margins, the vine bearing bunches of round, relatively small black-skinned grapes carrying a blue bloom, the meat of said grapes producing a gray-white juice of distinctive fruity and fresh flavor having a high sugar and high total acid content, maceration of the skins of said grapes producing an intense red coloration having substantially no blue coloration, said bunches being resistant to bunch rot.

No references cited.